(12) United States Patent
Chang

(10) Patent No.: US 11,865,170 B2
(45) Date of Patent: Jan. 9, 2024

(54) DNA VACCINE FOR HUMAN PAPILLOMAVIRUS AND METHOD FOR USING THE SAME

(71) Applicant: Papivax Biotech Inc., Taipei (TW)

(72) Inventor: Yung-Nien Chang, Elkridge, MD (US)

(73) Assignee: Papivax Biotech Inc., Taipei (TW)

( * ) Notice: Subject to any disclaimer, the term of this patent is extended or adjusted under 35 U.S.C. 154(b) by 150 days.

(21) Appl. No.: 17/534,256

(22) Filed: Nov. 23, 2021

(65) Prior Publication Data

US 2022/0160865 A1     May 26, 2022

Related U.S. Application Data

(60) Provisional application No. 63/117,473, filed on Nov. 24, 2020.

(51) Int. Cl.
| | |
|---|---|
| *A61K 39/12* | (2006.01) |
| *A61K 35/76* | (2015.01) |
| *A61K 39/00* | (2006.01) |
| *A61K 39/39* | (2006.01) |
| *A61P 31/20* | (2006.01) |
| *A61P 35/00* | (2006.01) |

(52) U.S. Cl.
CPC .............. *A61K 39/12* (2013.01); *A61K 35/76* (2013.01); *A61K 39/39* (2013.01); *A61P 35/00* (2018.01); *A61K 2039/53* (2013.01); *A61K 2039/55516* (2013.01); *A61K 2039/585* (2013.01)

(58) Field of Classification Search
CPC ................ A61K 39/12; A61K 2039/53; A61K 39/0011; A61K 2039/523; A61P 31/20
See application file for complete search history.

(56) References Cited

U.S. PATENT DOCUMENTS

| | | | |
|---|---|---|---|
| 8,187,606 | B2 | 5/2012 | Zhu et al. |
| 10,512,683 | B2 | 12/2019 | Chang |
| 10,555,996 | B2 | 2/2020 | Bunnik et al. |
| 2023/0226164 | A1 | 7/2023 | Chang |

FOREIGN PATENT DOCUMENTS

| | | | |
|---|---|---|---|
| WO | 2017070616 A2 | | 4/2017 |
| WO | WO2021113328 | * | 6/2021 |

OTHER PUBLICATIONS (Arribillage, L et al.). "Bivalent therapeutic vaccine against HPV16/18 genotypes consisting of a fusion protein between the extra domain A from human fibronectin and HPV16/18 E7 viral antigens." pp. 1-13, Journal for ImmunoTherapy of Cancer. vol. 8, No. 1, Jun. 24, 2020; abstract; p. 1, col. 1, paragraph 2; DOI: 10.1136/itc-2020-000704.

(Gan, L et al.). "Fusion of CTLA-4 with HPV16 E7 and E6 Enhanced the Potency of Therapeutic HPV DNA Vaccine." p. 1-7, PLOS One. vol. 9, No. 9. Sep. 29, 2014; p. 1, col. 2, paragraph 2, p. 7, col. 1, paragraph 1; DOI: 10.1371/journal.pone.0108892.

Cheng-Tao Lin, et al. A DNA vaccine encoding a codon-optimized human papillomavirus type 16 E6 gene enhances CTL response and anti-tumor activity, Journal of Biomedical Science vol. 13, No. 4, Apr. 29, 2006, p. 481-488.

* cited by examiner

*Primary Examiner* — Barry A Chestnut

(74) *Attorney, Agent, or Firm* — ScienBiziP, P.C.

(57) ABSTRACT

The present disclosure provides a DNA vaccine for a subject having a human papillomavirus (HPV)-associated disease. The DNA vaccine may include a DNA construct including a fusion gene. The fusion gene may be a subsegment of the DNA construct that includes an optimized HPV subsequence encoding at least one HPV antigen. The optimized HPV subsequence may include one or more of: an HPV-16 E6 expressing gene set forth in SEQ ID NO: 1, an HPV-16 E7 expressing gene set forth in SEQ ID NO: 2, an HPV-18 E6 expressing gene set forth in SEQ ID NO: 3, and an HPV-18 E7 expressing gene set forth in SEQ ID NO: 4.

10 Claims, 6 Drawing Sheets

Specification includes a Sequence Listing.

FIG. 1

SEQUENCE LISTING

<160> NUMBER OF SEQ ID NOS: 8

<210> SEQ ID NO 1
<211> LENGTH: 459
<212> TYPE: DNA
<213> ORGANISM: Artificial Sequence
<220> FEATURE:
<223> OTHER INFORMATION: Optimized HPV16 E6(detox) DNA sequence

<400> SEQUENCE: 1

```
atgcaccaga agaggacagc catgttccag gacccccagg agcggccgag gaagctgccc      60
caactgtgca ccgagctgca gacaaccatc cacgacatca tcctggagtg cgtgtactgc     120
aagcagcagc tgctgaggag agaggtctac gattttgcct ttagagacct gtgcattgtg     180
taccgggatg gcaacccata cgccgtgggg gataaatgtt tgaagttta cagcaagatt     240 tctgagtaca gacattactg ttattccctg tacggaacta cactggagca gcagtacaac     300
aagcccctgt gcgatctgct gattagatgc attaacggcc agaagccact gtgccctgag     360
gagaagcaga gacatctgga taagaagcag cggttccata acattagagg aagatggaca     420
ggcaggtgca tgtcatgctg cagaagctcc aggaccagg                            459
```

<210> SEQ ID NO 2
<211> LENGTH: 294
<212> TYPE: DNA
<213> ORGANISM: Artificial Sequence
<220> FEATURE:
<223> OTHER INFORMATION: Optimized HPV16 E7(detox) DNA sequence

<400> SEQUENCE: 2

```
atgcacgggg atacacccac actgcacgag tacatgctgg atctgcagcc cgagaccacc    60
gacctgtacg gctacggcca gctgaacgat tccagcgagg aggaggatga gattgacggg   120
cccgccggcc aggccgagcc cgatagggcc cactacaaca tcgtgacatt ctgctgcaag   180
tgcgatagca ccctgaggct gtgcgtccag agcacccacg tggacatcag gacactggag   240
gacctgctga tgggcaccct ggggatcgtg gggcccatct gcagccagaa gccc          294
```

<210> SEQ ID NO 3
<211> LENGTH: 459
<212> TYPE: DNA
<213> ORGANISM: Artificial Sequence
<220> FEATURE:
<223> OTHER INFORMATION: Optimized HPV18 E6(detox) DNA sequence

<400> SEQUENCE: 3

```
atggcccggt tgaggaccc cacaaggagg ccctacaagc tgcctgacct gtgcacagag    60
ctaaacacaa gcctccagga tattgagatc acctgcgtgt actgcaagac agtcctggag   120
ctgaccgagg tgttcgagtt cgcctttaag gatctgttcg tggtgtaccg ggatagcatc   180
ccccacgccg ccggccacaa gtgcatcgac ttctacagca ggatccggga gctgaggcac   240
tacagcgata gcgtgtacgg ggacacactg gagaagctga ccaacacagg gctgtacaac   300
ctgctgatcc ggtgcctgag ggggcagaag cccctgaacc cgccgagaa gctgaggcac   360 ctgaacgaga agaggcggtt ccacaacatc gccgggcact cagggggcca gtgccacagc   420
tgctgcaaca gggccaggca ggagaggctg cagcggcgc                          459
```

<210> SEQ ID NO 4
<211> LENGTH: 315
<212> TYPE: DNA
<213> ORGANISM: Artificial Sequence
<220> FEATURE:
<223> OTHER INFORMATION: Optimized HPV18 E7(detox) DNA sequence

<400> SEQUENCE: 4

```
atgcacggcc ctaaggccac cctgcaggac atcgtgctgc acctggagcc tcagaacgag    60
atccccgtgg acctgctggg gcacggccag ctgtccgatt ccgaggagga gaacgatgag   120
attgacggag tgaaccacca gcacctgcct gctaggaggg ccgaacccca gcggcacaca   180
atgctgtgca tgtgttgcaa gtgtgaggcc cggatcgagc tggtggtgga gagctcagcc   240
gatgacctgc gggccttcca gcagctgttc ctgaacacac tgagctttgt ggggccctgg   300
tgcgccagcc agcag                                                    315
```

<210> SEQ ID NO 5
<211> LENGTH: 3422
<212> TYPE: DNA
<213> ORGANISM: Artificial Sequence
<220> FEATURE:
<223> OTHER INFORMATION: pBI-11  DNA Sequence

<400> SEQUENCE: 5

```
atggcggccc ccggcgcccg gcggccgctg ctcctgctgc tgctggcagg ccttgcacat    60
ggcgcctcag cactctttga ggatctaatc atgcacgggg atacacccac actgcacgag   120
tacatgctgg atctgcagcc cgagaccacc gacctgtacg gctacggcca gctgaacgat   180
tccagcgagg aggaggatga gattgacggg cccgccggcc aggccgagcc cgatagggcc   240
cactacaaca tcgtgacatt ctgctgcaag tgcgatagca ccctgaggct gtgcgtccag   300
```

```
agcacccacg tggacatcag gacactggag gacctgctga tgggcaccct ggggatcgtg    360
gggcccatct gcagccagaa gcccatgcac ggccctaagg ccaccctgca ggacatcgtg    420
ctgcacctgg agcctcagaa cgagatcccc gtggacctgc tggggcacgg ccagctgtcc    480
gattccgagg aggagaacga tgagattgac ggagtgaacc accagcacct gcctgctagg    540
agggccgaac cccagcggca cacaatgctg tgcatgtgtt gcaagtgtga ggcccggatc    600
gagctggtgg tggagagctc agccgatgac ctgcgggcct ccagcagct gttcctgaac     660 acactgagct ttgtggggcc ctggtgcgcc agccagcaga tgcaccagaa gaggacagcc    720
atgttccagg accccagga gcggccgagg aagctgcccc aactgtgcac cgagctgcag     780
acaaccatcc acgacatcat cctggagtgc gtgtactgca agcagcagct gctgaggaga    840
gaggtctacg attttgcctt tagagacctg tgcattgtgt accgggatgg caacccatac    900
gccgtggggg ataaatgttt gaagttttac agcaagattt ctgagtacag acattactgt    960
tattccctgt acggaactac actggagcag cagtacaaca gcccctgtg cgatctgctg    1020 attagatgca ttaacggcca gaagccactg tgccctgagg agaagcagag acatctggat   1080
aagaagcagc ggttccataa cattagagga gatggacag gcaggtgcat gtcatgctgc   1140
agaagctcca ggaccaggat ggcccggttt gaggacccca aaggaggcc ctacaagctg    1200 cctgacctgt gcacagagct aaacacaagc ctccaggata ttgagatcac ctgcgtgtac   1260
tgcaagacag tcctggagct gaccgaggtg ttcgagttcg cctttaagga tctgttcgtg   1320
gtgtaccggg atagcatccc ccacgccgcc ggccacaagt gcatcgactt ctacagcagg   1380
atccgggagc tgaggcacta cagcgatagc gtgtacgggg acacactgga gaagctgacc   1440
aacacagggc tgtacaacct gctgatccgg tgcctgaggg ggcagaagcc cctgaacccc   1500
gccgagaagc tgaggcacct gaacgagaag aggcggttcc acaacatcgc cgggcactac   1560
aggggccagt gccacagctg ctgcaacagg gccaggcagg agaggctgca gcggcgcatg   1620
gctcgtgcgg tcgggatcga cctcgggacc accaactccg tcgtctcggt tctgaaggt    1680 ggcgacccgg tcgtcgtcgc caactccgag ggctccagga ccacccccgtc aattgtcgcg   1740 ttcgcccgca acggtgaggt gctggtcggc cagcccgcca agaaccaggc ggtgaccaac   1800
gtcgatcgca ccgtgcgctc ggtcaagcga cacatgggca gcgactggtc catagagatt   1860
gacggcaaga aatacaccgc gccggagatc agcgcccgca ttctgatgaa gctgaagcgc   1920
gacgccgagg cctacctcgg tgaggacatt accgacgcgg ttatcacgac gcccgcctac   1980
ttcaatgacg cccagcgtca ggccaccaag gacgccggcc agatcgccgg cctcaacgtg   2040
ctgcggatcg tcaacgagcc gaccgcggcc gcgctggcct acggcctcga caagggcgag   2100
aaggagcagc gaatcctggt cttcgacttg ggtggtggca cttcgacgt tccctgctg    2160 gagatcggcg agggtgtggt tgaggtccgt gccacttcgg gtgacaacca cctcggcggc   2220
gacgactggg accagcgggt cgtcgattgg ctggtggaca gttcaaggg caccagcggc   2280 atcgatctga ccaaggacaa gatggcgatg cagcggctgc gggaagccgc cgagaaggca   2340
aagatcgagc tgagttcgag tcagtccacc tcgatcaacc tgccctacat caccgtcgac   2400
gccgacaaga cccgttgtt cttagacgag cagctgaccc gcgcggagtt caacgcggatc   2460 actcaggacc tgctggaccg cactcgcaag ccgttccagt cggtgatcgc tgacaccggc   2520
atttcggtgt cggagatcga tcacgttgtg ctcgtgggtg gttcgacccg gatgccgcg    2580 gtgaccgatc tggtcaagga actcaccggc ggcaaggaac ccaacaaggg cgtcaacccc   2640
gatgaggttg tcgcggtggg agccgctctg caggccggcg tcctcaaggg cgaggtgaaa   2700
```

| | |
|---|---|
| gacgttctgc tgcttgatgt taccccgctg agcctgggta tcgagaccaa gggcggggtg | 2760 |
| atgaccaggc tcatcgagcg caacaccacg atccccacca agcggtcgga gactttcacc | 2820 |
| accgccgacg acaaccaacc gtcggtgcag atccaggtct atcaggggga gcgtgagatc | 2880 |
| gccgcgcaca acaagttgct cgggtccttc gagctgaccg gcatcccgcc ggcgccgcgg | 2940 |
| gggattccgc agatcgaggt cactttcgac atcgacgcca acggcattgt gcacgtcacc | 3000 |
| gccaaggaca agggcaccgg caaggagaac acgatccgaa tccaggaagg ctcgggcctg | 3060 |
| tccaaggaag acattgaccg catgatcaag gacgccgaag cgcacgccga ggaggatcgc | 3120 |
| aagcgtcgcg aggaggccga tgttcgtaat caagccgaga cattggtcta ccagacggag | 3180 |
| aagttcgtca agaacagcg tgaggccgag ggtggttcga aggtacctga agacacgctg | 3240 |
| aacaaggttg atgccgcggt ggcggaagcg aaggcggcac ttggcggatc ggatatttcg | 3300 |
| gccatcaagt cggcgatgga gaagctgggc caggagtcgc aggctctggg gcaagcgatc | 3360 |
| tacgaagcag ctcaggctgc gtcacaggcc actggcgctg cccaccccgg ctcggctgat | 3420 |
| ga | 3422 |

<210> SEQ ID NO 6
<211> LENGTH: 3422
<212> TYPE: DNA
<213> ORGANISM: Artificial Sequence
<220> FEATURE:
<223> OTHER INFORMATION: pBI-12 DNA Sequence

<400> SEQUENCE: 6

| | |
|---|---|
| atggccgccc caggagctag aaggccactt ttgttgctgt tgctggccgg attagcccat | 60 |
| ggagctagcg ctctgtttga ggatctgatc atgcacgggg atacccacac actgcacgag | 120 |
| tacatgctgg atctgcagcc cgagaccacc gacctgtacg gctacggcca gctgaacgat | 180 |
| tccagcgagg aggaggatga gattgacggg cccgccggcc aggccgagcc cgatagggcc | 240 |
| cactacaaca tcgtgacatt ctgctgcaag tgcgatagca ccctgaggct gtgcgtccag | 300 |
| agcacccacg tggacatcag gacactggag gacctgctga tgggcaccct ggggatcgtg | 360 |
| gggcccatct gcagccagaa gcccatgcac ggccctaagg ccaccctgca ggacatcgtg | 420 |
| ctgcacctgg agcctcagaa cgagatcccc gtggacctgc tggggcacgg ccagctgtcc | 480 |
| gattccgagg aggagaacga tgagattgac ggagtgaacc accagcacct gcctgctagg | 540 |
| agggccgaac cccagcggca cacaatgctg tgcatgtgtt gcaagtgtga ggcccggatc | 600 |
| gagctggtgg tggagagctc agccgatgac ctgcgggcct tccagcagct gttcctgaac | 660 |
| acactgagct tgtggggcc ctggtgcgcc agccagcaga tgcaccagaa gaggacagcc | 720 |
| atgttccagg accccagga gcggccgagg aagctgcccc aactgtgcac cgagctgcag | 780 |
| acaaccatcc acgacatcat cctggagtgc gtgtactgca gcagcagct gctgaggaga | 840 |
| gaggtctacg atttgccctt tagagacctg tgcattgtgt accggatgg caacccatac | 900 |
| gccgtggggg ataaatgttt gaagttttac agcaagattt ctgagtacag acattactgt | 960 |
| tattccctgt acggaactac actggagcag cagtacaaca gcccctgtg cgatctgctg | 1020 |
| attagatgca ttaacggcca gaagccactg tgccctgagg agaagcagag acatctggat | 1080 |
| aagaagcagc ggttccataa cattagagga agatggacag gcaggtgcat gtcatgctgc | 1140 |
| agaagctcca ggaccaggat ggcccggttt gaggacccca caaggaggcc ctacaagctg | 1200 |
| cctgacctgt gcacagagct aaacacaagc ctccaggata ttgagatcac ctgcgtgtac | 1260 |

```
tgcaagacag tcctggagct gaccgaggtg ttcgagttcg cctttaagga tctgttcgtg      1320
gtgtaccggg atagcatccc ccacgccgcc ggccacaagt gcatcgactt ctacagcagg      1380 atccggggagc tgaggcacta cagcgatagc gtgtacgggg acacactgga gaagctgacc    1440
aacacagggc tgtacaacct gctgatccgg tgcctgaggg ggcagaagcc cctgaacccc     1500
gccgagaagc tgaggcacct gaacgagaag aggcggttcc acaacatcgc cgggcactac    1560
aggggccagt gccacagctg ctgcaacagg gccaggcagg agaggctgca gcggcgcatg    1620
gctcgtgcgg tcgggatcga cctcgggacc accaactccg tcgtctcggt tctggaaggt    1680
ggcgacccgg tcgtcgtcgc caactccgag ggctccagga ccaccccgtc aattgtcgcg    1740
ttcgcccgca acggtgaggt gctggtcggc cagcccgcca agaaccaggc ggtgaccaac    1800
gtcgatcgca ccgtgcgctc ggtcaagcga cacatgggca cgactggtc catagagatt     1860 gacggcaaga atacaccgc gccggagatc agcgcccgca ttctgatgaa gctgaagcgc     1920
gacgccgagg cctacctcgg tgaggacatt accgacgcgg ttatcacgac gcccgcctac    1980
ttcaatgacg cccagcgtca ggccaccaag gacgccggcc agatcgccgg cctcaacgtg    2040
ctgcggatcg tcaacgagcc gaccgcggcc gcgctggcct acggcctcga caagggcgag    2100
aaggagcagc gaatcctggt cttcgacttg ggtggtggca ctttcgacgt ttccctgctg    2160
gagatcggcg agggtgtggt tgaggtccgt gccacttcgg gtgacaacca cctcggcggc    2220
gacgactggg accagcgggt cgtcgattgg ctggtggaca agttcaaggg caccagcggc    2280
atcgatctga ccaaggacaa gatggcgatg cagcggctgc gggaagccgc cgagaaggca    2340
aagatcgagc tgagttcgag tcagtccacc tcgatcaacc tgccctacat caccgtcgac    2400
gccgacaaga acccgttgtt cttagacgag cagctgaccc gcgcggagtt ccaacggatc    2460
actcaggacc tgctggaccg cactcgcaag ccgttccagt cggtgatcgc tgacaccggc    2520
atttcggtgt cggagatcga tcacgttgtg ctcgtgggtg gttcgacccg gatgcccgcg    2580
gtgaccgatc tggtcaagga actcaccggc ggcaaggaac ccaacaaggg cgtcaacccc    2640
gatgaggttg tcgcggtggg agccgctctg caggccggcg tcctcaaggg cgaggtgaaa    2700
gacgttctgc tgcttgatgt taccccgctg agcctgggta tcgagaccaa gggcggggtg    2760
atgaccaggc tcatcgagcg caacaccacg atccccacca agcggtcgga gactttcacc    2820
accgccgacg caaccaacc gtcggtgcag atccaggtct atcagggga gcgtgagatc      2880 gccgcgcaca acaagttgct cgggtccttc gagctgaccg gcatcccgcc ggcgccgcgg    2940
gggattccgc agatcgaggt cactttcgac atcgacgcca acggcattgt gcacgtcacc    3000
gccaaggaca agggcaccgg caaggagaac acgatccgaa tccaggaagg ctcgggcctg    3060
tccaaggaag acattgaccg catgatcaag gacgccgaag cgcacgccga ggaggatcgc    3120
aagcgtcgcg aggaggccga tgttcgtaat caagccgaga cattggtcta ccagacggag    3180
aagttcgtca agaacagcg tgaggccgag ggtggttcga aggtacctga agacacgctg     3240
aacaaggttg atgccgcgt ggcggaagcg aaggcggcac ttggcggatc ggatatttcg     3300
gccatcaagt cggcgatgga gaagctgggc caggagtcgc aggctctggg gcaagcgatc    3360
tacgaagcag ctcaggctgc gtcacaggcc actggcgctg cccaccccgg ctcggctgat    3420
ga                                                                     3422
```

<210> SEQ ID NO 7
<211> LENGTH: 3421
<212> TYPE: DNA
<213> ORGANISM: Artificial Sequenc
<220> FEATURE:
<223> OTHER INFORMATION: pBI-10.1 DNA sequence

<400> SEQUENCE: 7

```
atggcggccc ccggcgcccg gcggccgctg ctcctgctgc tgctggcagg ccttgcacat      60
ggcgcctcag cactctttga ggatctaatc atgcatggag atacacctac attgcatgaa    120
tatatgttag atttgcaacc agagacaact gatctctacg gttatgggca attaaatgac    180
agctcagagg aggaggatga aatagatggt ccagctggac aagcagaacc ggacagagcc    240
cattacaata ttgttacctt ttgttgcaag tgtgactcta cgcttcggtt gtgcgtacaa    300
agcacacacg tagacattcg tactttggaa gacctgttaa tgggcacact aggaattgtg    360
ggccccatct gttctcaaaa gccgatgcat ggacctaagg caacattgca agacattgta    420
ttgcatttag agccccaaaa tgaaattccg gttgaccttc taggtcacgg caattaagc     480
gactcagagg aagaaaacga tgaaatagat ggagttaatc atcaacattt accagcccga    540
cgagccgaac cacaacgtca cacaatgttg tgtatgtgtt gtaagtgtga agccagaatt    600
gagctagtag tagaaagctc agcagacgac cttcgagcat ccagcagct gtttctgaac     660
accctgtcct ttgtgggtcc gtggtgtgca tcccagcaga tgcaccaaaa gagaactgca    720
atgtttcagg acccacagga gcgacccaga aagttaccac agttatgcac agagctgcaa    780
acaactatac atgatataat attagaatgt gtgtactgca agcaacagtt actgcgacgt    840
gaggtatatg actttgcttt tcgggattta tgcatagtat atagagatgg gaatccatat    900
gctgtaggtg ataaatgttt aaagttttat tctaaaatta gtgagtatag acattattgt    960
tatagtttgt atggaacaac attagaacag caatacaaca aaccgttgtg tgatttgtta   1020
attaggtgta ttaacggtca aaagccactg tgtcctgaag aaaagcaaag acatctggac   1080
aaaaagcaaa gattccataa tataagggggt cggtggaccg gtcgatgtat gtcttgttgc   1140
agatcatcaa gaacacgatg gcgcgctttg aggatccaac acggcgaccc tacaagctac   1200
ctgatctgtg cacggaactg aacacttcac tgcaagacat agaaataacc tgtgtatatt   1260
gcaagacagt attggaactt acagaggtat ttgaatttgc atttaaagat ttatttgtgg   1320
tgtatagaga cagtataccg catgctgcag gccataaatg tatagatttt tattctagaa   1380
ttagagaatt aagacattat tcagactctg tgtatggaga cacattggaa aaactaacta   1440
acactgggtt atacaattta ttaataaggt gcctgcgggg ccagaaaccg ttgaatccag   1500
cagaaaaact tagacacctt aatgaaaaac gacgatttca caacatagct gggcactata   1560
gaggccagtg ccattcgtgc tgcaaccgag cacgacagga acgactccaa cgacgcatgg   1620
ctcgtgcggt cggatcgac ctcgggacca ccaactccgt cgtctcggtt ctggaaggtg    1680
gcgacccggt cgtcgtcgcc aactccgagg gctccaggac caccccgtca attgtcgcgt   1740
tcgcccgcaa cggtgaggtg ctggtcggcc agcccgccaa gaaccaggcg gtgaccaacg   1800
tcgatcgcac cgtgcgctcg gtcaagcgac acatgggcag cgactggtcc atagagattg   1860
acggcaagaa atacaccgcg ccggagatca gcgcccgcat tctgatgaag ctgaagcgcg   1920
acgccgaggc ctacctcggt gaggacatta ccgacgcggt tatcacgacg cccgcctact   1980
tcaatgacgc ccagcgtcag gccaccaagg acgccggcca gatcgccggc tcaacgtgc    2040
tgcggatcgt caacgagccg accgcggccg cgctggccta cggcctcgac aagggcgaga   2100
aggagcagcg aatcctggtc ttcgacttgg gtggtgcac tttcgacgtt tccctgctgg   2160
agatcggcga gggtgtggtt gaggtccgtg ccacttcggg tgacaaccac ctcggcggcg   2220
```

```
acgactggga ccagcgggtc gtcgattggc tggtggacaa gttcaagggc accagcggca    2280
tcgatctgac caaggacaag atggcgatgc agcggctgcg ggaagccgcc gagaaggcaa    2340
agatcgagct gagttcgagt cagtccacct cgatcaacct gccctacatc accgtcgacg    2400
ccgacaagaa cccgttgttc ttagacgagc agctgaccog cgcggagttc caacggatca    2460
ctcaggacct gctggaccgc actcgcaagc cgttccagtc ggtgatcgct gacaccggca    2520
tttcggtgtc ggagatcgat cacgttgtgc tcgtgggtgg ttcgacccgg atgcccgcgg    2580
tgaccgatct ggtcaaggaa ctcaccggcg gcaaggaacc caacaagggc gtcaaccccg    2640
atgaggttgt cgcggtggga gccgctctgc aggccggcgt cctcaagggc gaggtgaaag    2700
acgttctgct gcttgatgtt accccgctga gcctgggtat cgagaccaag ggcggggtga    2760
tgaccaggct catcgagcgc aacaccacga tccccaccaa gcggtcggag actttcacca    2820
ccgccgacga caaccaaccg tcggtgcaga tccaggtcta tcaggggag cgtgagatcg    2880
ccgcgcacaa caagttgctc gggtccttcg agctgaccgg catcccgccg cgcgccgcgg    2940
ggattccgca gatcgaggtc actttcgaca tcgacgccaa cggcattgtg cacgtcaccg    3000
ccaaggacaa gggcaccggc aaggagaaca cgatccgaat ccaggaaggc tcgggcctgt    3060
ccaaggaaga cattgaccgc atgatcaagg acgccgaagc gcacgccgag gaggatcgca    3120
agcgtcgcga ggaggccgat gttcgtaatc aagccgagac attggtctac cagacggaga    3180
agttcgtcaa agaacagcgt gaggccgagg gtggttcgaa ggtacctgaa gacacgctga    3240
acaaggttga tgccgcggtg gcggaagcga aggcggcact ggcggatcg gatatttcgg    3300
ccatcaagtc ggcgatggag aagctgggcc aggagtcgca ggctctgggg caagcgatct    3360
acgaagcagc tcaggctgcg tcacaggcca ctggcgctgc ccaccccggc tcggctgatg    3420
a                                                                    3421
```

<210> SEQ ID NO 8
<211> LENGTH: 2189
<212> TYPE: DNA
<213> ORGANISM: Artificial Sequence
<220> FEATURE:
<223> OTHER INFORMATION: pBI-1 (pNGVL4a-sigE7(detox)HSP70) DNA Sequence

<400> SEQUENCE: 8

```
atggcggccc ccggcgcccg gcggccgctg ctcctgctgc tgctggcagg ccttgcacat     60
ggcgcctcag cactctttga ggatctaatc atgcatggag atacacctac attgcatgaa    120
tatatgttag atttgcaacc agagacaact gatctctacg ttatgggca attaaatgac    180
agctcagagg aggaggatga aatagatggt ccagctggac aagcagaacc ggacagagcc    240
cattacaata ttgtaacctt ttgttgcaag tgtgactcta cgcttcggtt gtgcgtacaa    300
agcacacacg tagacattcg tactttggaa gacctgttaa tgggcacact aggaattgtg    360
tgccccatct gttctcaagg atccatggct cgtgcggtcg gatcgacct cgggaccacc    420
aactccgtcg tctcggttct ggaaggtggc gacccgtcg tcgtcgccaa ctccgagggc    480
tccaggacca ccccgtcaat tgtcgcgttc gcccgcaacg gtgaggtgct ggtcggccag    540
cccgccaaga ccaggcggt gaccaacgtc gatcgcaccg tgcgctcggt caagcgacac    600
atgggcagcg actggtccat agagattgac ggcaagaaat acaccgcgcc ggagatcagc    660
gcccgcattc tgatgaagct gaagcgcgac gccgaggcct acctcggtga ggacattacc    720
gacgcggtta tcacgacgcc cgcctacttc aatgacgccc agcgtcaggc caccaaggac    780
gccggccaga tcgccggcct caacgtgctg cggatcgtca acgagccgac gcggccgcg    840
```

```
ctggcctacg gcctcgacaa gggcgagaag gagcagcgaa tcctggtctt cgacttgggt    900
ggtggcactt tcgacgtttc cctgctggag atcggcgagg gtgtggttga ggtccgtgcc    960
acttcgggtg acaaccacct cggcggcgac gactgggacc agcgggtcgt cgattggctg   1020
gtggacaagt tcaagggcac cagcggcatc gatctgacca aggacaagat ggcgatgcag   1080
cggctgcggg aagccgccga gaaggcaaag atcgagctga gttcgagtca gtccacctcg   1140
atcaacctgc cctacatcac cgtcgacgcc gacaagaacc cgttgttctt agacgagcag   1200
ctgacccgcg cggagttcca acggatcact caggacctgc tggaccgcac tcgcaagccg   1260
ttccagtcgg tgatcgctga caccggcatt tcggtgtcgg agatcgatca cgttgtgctc   1320
gtgggtggtt cgacccggat gcccgcggtg accgatctgg tcaaggaact caccggcggc   1380
aaggaaccca acaagggcgt caaccccgat gaggttgtcg cggtgggagc cgctctgcag   1440
gccggcgtcc tcaagggcga ggtgaaagac gttctgctgc ttgatgttac cccgctgagc   1500
ctgggtatcg agaccaaggg cggggtgatg accaggctca tcgagcgcaa caccacgatc   1560
cccaccaagc ggtcggagac tttcaccacc gccgacgaca accaaccgtc ggtgcagatc   1620
caggtctatc aggggagcg tgagatcgcc gcgcacaaca agttgctcgg gtccttcgag   1680
ctgaccggca tcccgccggc gccgcggggg attccgcaga tcgaggtcac tttcgacatc   1740
gacgccaacg gcattgtgca cgtcaccgcc aaggacaagg gcaccggcaa ggagaacacg   1800
atccgaatcc aggaaggctc gggcctgtcc aaggaagaca ttgaccgcat gatcaaggac   1860
gccgaagcgc acgccgagga ggatcgcaag cgtcgcgagg aggccgatgt tcgtaatcaa   1920
gccgagacat tggtctacca gacggagaag ttcgtcaaag aacagcgtga ggccgagggt   1980
ggttcgaagg tacctgaaga cacgctgaac aaggttgatg ccgcggtggc ggaagcgaag   2040
gcggcacttg gcggatcgga tatttcggcc atcaagtcgg cgatggagaa gctgggccag   2100
gagtcgcagg ctctggggca agcgatctac gaagcagctc aggctgcgtc acaggccact   2160
ggcgctgccc accccggctc ggctgatga                                     2189
```

DNA VACCINE FOR HUMAN PAPILLOMAVIRUS AND METHOD FOR USING THE SAME

CROSS-REFERENCE TO RELATED APPLICATION

This application claims the benefit of and priority to U.S. Provisional Patent Application No. 63/117,473, filed Nov. 24, 2020, and entitled "HUMAN PAPILLOMAVIRUS DNA VACCINE," which is hereby fully incorporated by reference herein.

REFERENCE TO SEQUENCE LISTING

Accompanying this application is a sequence listing in an American Standard Code for Information Interchange (ASCII) text file named "220107-137111-sequence-listing-v1F", created Jan. 7, 2022, and having a size of 19,844 bytes. The sequence listing is hereby fully incorporated by reference herein.

BACKGROUND

1. Field

The present disclosure generally relates to DNA vaccines, particularly for an HPV-associated disease, and more specifically to improving the DNA vaccine through codon optimization.

2. Related Art

Human papillomavirus (HPV) is a common etiological agent in several human cancers, including cervical, anal, penile, vulvar, vaginal, and head and neck cancers. Current vaccines against HPV, such as Gardasil® and Cervarix®, have shown clinical efficacy in preventing HPV infection, but they are ineffective in treating patients with existing HPV infection or HPV-associated cancers. As such, development of therapeutic vaccines for patients infected with HPV or even suffering from HPV-associated diseases are highly demanded.

Deoxyribonucleic acid (DNA) vaccination is a technique for protecting against infection or treating disease by injection with a genetically engineered plasmid containing a DNA sequence encoding one or more antigens. DNA vaccines have theoretical advantages over conventional vaccines, including safety, speed, and predictability of manufacture; temperature stability; flexibility in design; and the ability to induce a wider range of immune response types. Despite the advantages described above, DNA vaccines generally have obstacles to induce strong antigen-specific immune responses in animals. For example, DNA vaccination with HPV E6 and E7 genes may be poorly immunogenic because the virus has evolved mechanisms to evade host recognition, including low levels of E6/E7 expression. Therefore, a large number of different strategies to enhance DNA vaccine immunogenicity have been tested, including vector design improvement, antigen codon optimization, use of traditional adjuvant and molecular adjuvants, electroporation (EP), co-expression of molecular adjuvants and prime-boost strategies (L. Li and N. Petrovsky, *Expert Rev Vaccines.* 2016; 15(3):313-29).

Codon optimization refers to approaches using synonymous mutations to increase protein expression of an interested gene, such as the antigen-expressing gene in the DNA vaccine. However, codon optimization does not always positively correlate with DNA vaccine efficacy. Many studies have shown that rare codons may not always be a speed-limiting step and frequently used codons do not guarantee increased protein production. Moreover, coding regions not only specify amino acid sequences, but often also contain overlapping genetic information which includes RNA secondary structures that can affect protein folding. It is indicated that synonymous codons could potentially change protein conformation and function (L. Li and N. Petrovsky, *Expert Rev Vaccines.* 2016; 15(3):313-29, V. P. Mauro and S. A. Chappell, *Methods Mol Biol.* 2018; 1850: 275-288). Accordingly, using codon optimization to enhance expression of encoded antigens in DNA vaccines may cause unexpected detrimental results and requires careful consideration. Further, it is even more difficult to predict whether a DNA vaccine comprising codon-optimized sequences can achieve a desired immunogenicity.

In view of the reasons mentioned above, there exists an unmet need for providing a DNA vaccine with better efficacy in treating HPV-associated diseases. However, improving the efficacy of DNA vaccines against HPV-associated diseases by way of codon optimization is still highly unpredictable and thus remains a problem to be solved in the field.

BRIEF SUMMARY OF THE DISCLOSURE

In some embodiments of the present disclosure, a DNA vaccine for a subject having a human papillomavirus (HPV)-associated disease may be provided. The DNA vaccine may include a DNA construct including a fusion gene. The fusion gene may be a subsegment of the DNA construct that includes an optimized HPV subsequence encoding at least one HPV antigen. The optimized HPV subsequence may include one or more of: an HPV-16 E6 expressing gene set forth in SEQ ID NO: 1, an HPV-16 E7 expressing gene set forth in SEQ ID NO: 2, an HPV-18 E6 expressing gene set forth in SEQ ID NO: 3, and an HPV-18 E7 expressing gene set forth in SEQ ID NO: 4.

In some embodiments, the fusion gene may further include a subsequence encoding an immunostimulant.

In some embodiments, the immunostimulant may be a 70 kilodalton (kDa) heat shock protein (HSP70) or a human calreticulin (CRT) protein.

In some embodiments, the optimized HPV subsequence may include the HPV-16 E6, HPV-16 E7, HPV-18 E6, and HPV-18 E7 expressing gene, and the fusion gene may include SEQ ID NO: 5.

In some embodiments, the fusion gene may further include an optimized signal sequence, and the fusion gene may include SEQ ID NO: 6.

Another aspect of present disclosure may provide a method for treating an HPV-associated disease in a subject in need thereof. The method may include administering the aforementioned DNA vaccine to the subject.

In some embodiments, the method may further include administering a recombinant vaccinia virus expressing E6 and E7 of both HPV-16 and HPV-18 to the subject, where the DNA vaccine is administered as a priming vaccine and the recombinant vaccinia virus expressing E6 and E7 of both HPV-16 and HPV-18 is administered as a boosting vaccine.

In some embodiments, the recombinant vaccinia virus expressing E6 and E7 of both HPV-16 and HPV-18 may be TA-HPV.

In some embodiments, the TA-HPV may be administered at a dose ranging from $1 \times 10^4$ plaque-forming units (pfu) to $2 \times 10^8$ pfu.

In some embodiments, the DNA vaccine may be administered at a dose ranging from 100 micrograms per subject to 20 milligrams per subject.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIG. 1 is a schematic illustration showing DNA constructs according to some embodiments of the present disclosure.

In accordance with common practice, the various described features are not drawn to scale and are drawn to emphasize features relevant to the present disclosure. Like reference characters denote like elements throughout the figures and text.

DETAILED DESCRIPTION

Figure 2:
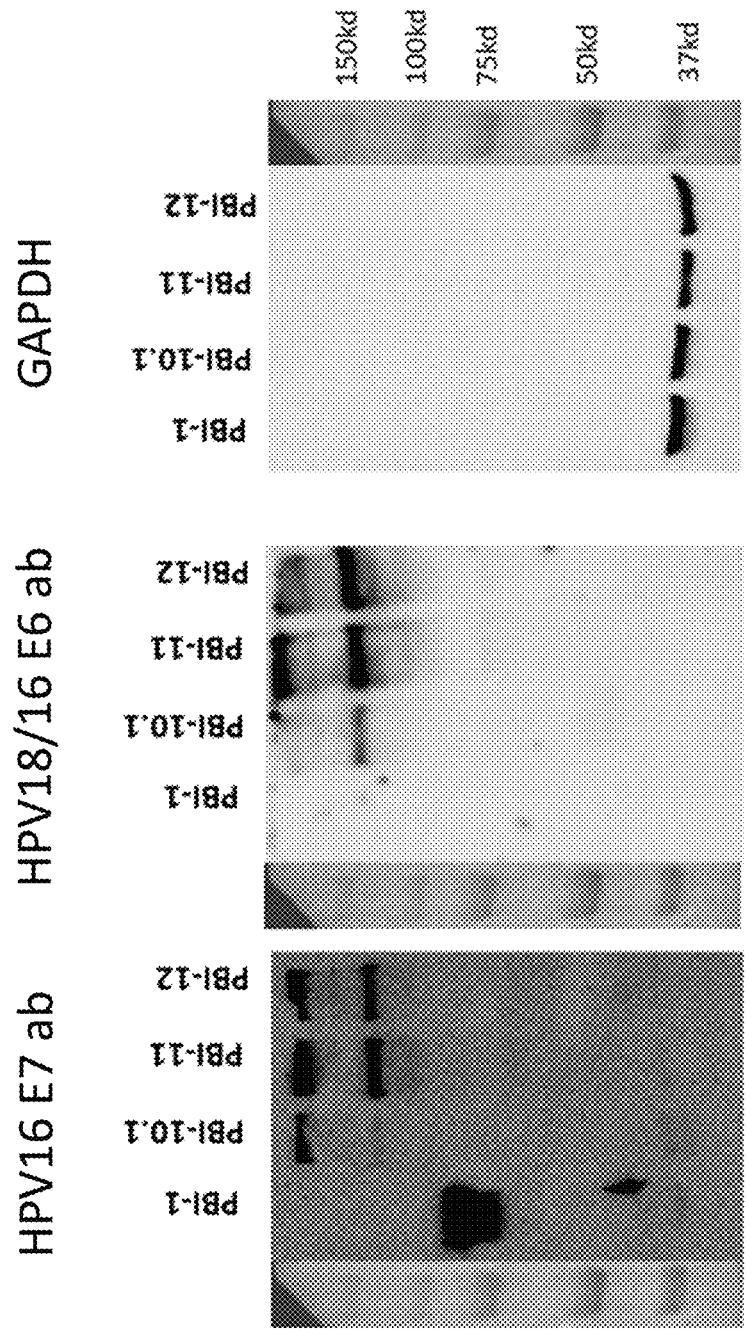
FIG. 2 is a western blot image showing the HPV antigen expression level in Human Embryonic Kidney (HEK) 293 cells transfected with either pBI-1, pBI-10.1, pBI-11, or pBI-12, in accordance with an embodiment of the present disclosure.

The present disclosure will now be described more fully hereinafter with reference to the accompanying drawings, in which exemplary embodiments of the disclosure are shown. This disclosure may, however, be embodied in many different forms and should not be construed as limited to the exemplary embodiments set forth herein. Rather, these exemplary embodiments are provided so that this disclosure will be thorough and complete, and will fully convey the scope of the disclosure to those skilled in the art. Like reference numerals refer to like elements throughout.

The terminology used herein is for the purpose of describing particular exemplary embodiments only and is not intended to be limiting of the disclosure. As used herein, the singular forms "a", "an", and "the" are intended to include the plural forms as well, unless the context clearly indicates otherwise. It will be further understood that the terms "comprises" and/or "comprising," or "includes" and/or "including" or "has" and/or "having", when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

A DNA vaccine of the present disclosure is provided for a subject having a human papillomavirus (HPV)-associated disease. The subject having an HPV-associated disease may be a mammal (e.g., human, mice, etc.) suffering from, but not limited to, warts, papilloma, intraepithelial neoplasia, penile cancer, vaginal cancer, vulva cancer, anal cancer, oropharyngeal cancer, non-melanoma skin cancer, conjunctival cancer, or cervical cancer.

The DNA vaccine may include a DNA construct including a fusion gene, wherein the fusion gene includes a human papillomavirus (HPV) subsequence having been codon-optimized. The DNA vaccine may also be called an optimized DNA vaccine in the context described herein.

A synthetic fusion gene including a codon-optimized subsequence encoding at least one HPV antigen (e.g., an optimized HPV subsequence) may be provided. Specifically, the optimized HPV subsequence may include one or more of: an HPV-16 E6 expressing gene that encodes HPV-16 E6 antigen set forth in SEQ ID NO:1; an HPV-16 E7 expressing gene that encodes HPV-16 E7 antigen set forth in SEQ ID NO: 2; an HPV-18 E6 expressing gene that encodes HPV-18

E6 antigen set forth in SEQ ID NO: 3, and an HPV-18 E7 expressing gene that encodes HPV-18 E7 antigen set forth in SEQ ID NO: 4.

In some embodiments, the fusion gene may be cloned to a pNGVL4a plasmid, which is functioned as a vector, to provide a DNA construct, and the fusion gene therefore may become a subsegment of the DNA construct. In further embodiments, alternative and/or additional plasmids may be used to provide a vector described herein.

In some embodiments, the DNA vaccine may further include an ingredient, such as an adjuvant, to create a stronger immune response in the subject receiving the vaccine.

In some embodiments, the DNA vaccine may be administered as a priming vaccine and a recombinant vaccinia virus expressing E6 and E7 of both HPV-16 and HPV-18 may be administered subsequently as a boosting vaccine, so as to provide a combination therapy being used in a heterologous prime-boost regimen to enhance a subject's immune responses against HPV-associated diseases. For example, the DNA vaccine may be administered at a dose ranging from 100 micrograms per subject to 20 milligrams per subject, and the recombinant vaccinia virus expressing E6 and E7 of both HPV-16 and HPV-18 may be administered at a dose ranging from $1 \times 10^4$ pfu to $2 \times 10^8$ pfu.

In some embodiments, the recombinant vaccinia virus expressing E6 and E7 of both HPV-16 and HPV-18 may be TA-HPV. TA-HPV is a recombinant vaccinia viral vaccine expressing oncogenes E6 and E7 of HPV types 16 and 18. The HPV-16 and HPV-18 oncogenes E6 and E7 may be inserted in a head-to-head orientation under the control of the p7.5 and H6 promoters at a neutral site in the vaccinia virus Wyeth strain genome (L. K. Borysiewicz et al., *Lancet.*, 1996 Jun. 1; 347(9014):1523-7). For both the HPV-16 and HPV-18 genes, the E6 termination codon may be altered to create an E6/E7 fused open reading frame and defined mutation introduced to inactivate the Rb-binding site in E7. The TA-HPV may be administered at a dose ranging from $1 \times 10^4$ pfu to $2 \times 10^8$ pfu. The TA-HPV may be administered preferably at a dose ranging from $2 \times 10^4$ pfu to $5 \times 10^7$ pfu.

Figure 1:
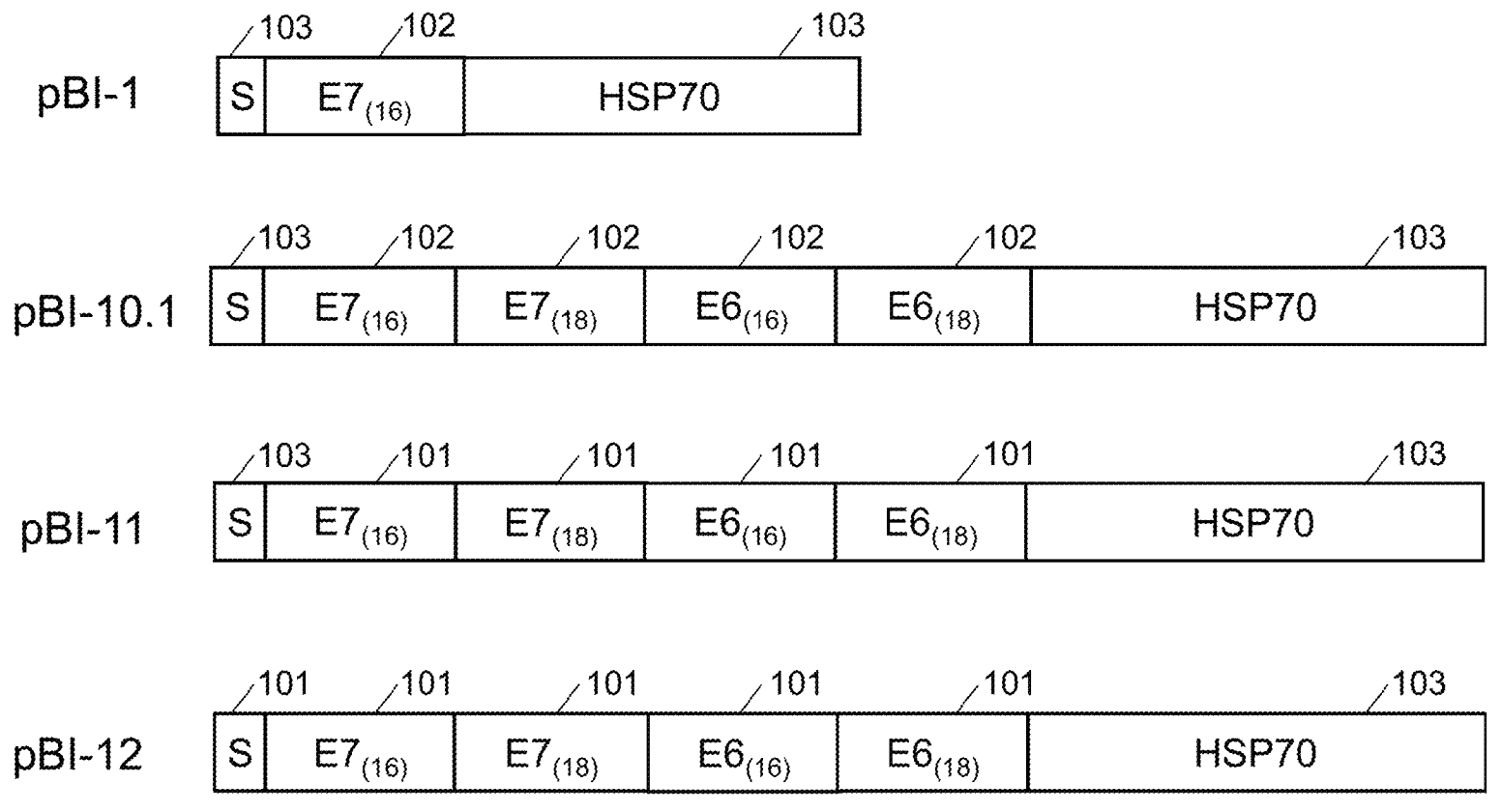

Examples of the DNA constructs of the DNA vaccines are described as follows. FIG. 1 illustrates four different DNA constructs (pBI-1, pBI-10.1, pBI-11, and pBI-12). Each DNA construct includes a fusion gene that includes a subsequence encoding a signal peptide (denoted as "S" in FIG. 1), a subsequence encoding an immunostimulant (e.g., HSP70 in FIG. 1), and a subsequence encoding one or more HPV antigens (e.g., HPV-16 E7 (or $E7_{(16)}$ in FIG. 1), HPV-18 E7 (or $E7_{(18)}$ in FIG. 1), HPV-16 E6 (or $E6_{(16)}$ in FIG. 1), and/or HPV-18 E6 (or $E6_{(18)}$ in FIG. 1)). In some embodiments, the immunostimulant may include, but is not limited to, a 70 kilodalton heat shock protein (HSP70) or a human calreticulin (CRT) protein.

In some embodiments, pBI-1, which has a nucleotide sequence set forth in SEQ ID NO: 8, is a DNA construct including a fusion gene which includes: a subsequence encoding a signal peptide, an HPV subsequence encoding a "detox" form of HPV-16 E7 expressing gene, and a subsequence encoding an HSP70. The term "detox" means the HPV oncogenes (e.g., E6 or E7) DNA are modified by mutation to express proteins that are incapable of oncogenic transformation. In some embodiments, pBI-10.1, which has a nucleotide sequence set forth in SEQ ID NO: 7, is a DNA construct including a fusion gene which includes: a subsequence encoding a signal peptide; an HPV subsequence encoding a "detox" form of HPV-16 E7 expressing gene, a "detox" form of HPV-18 E7 expressing gene, a "detox" form of HPV-16 E6 expressing gene, and a "detox" form of HPV-18 E6 expressing gene; and a subsequence encoding an HSP70.

To increase the expression of HPV antigens and further achieve DNA vaccines against HPV-associated diseases with safety and improved immunogenicity, optimized HPV subsequences respectively encoding HPV-16 E6, HPV-16 E7, HPV-18 E6, and HPV-18 E7 may be designed by mutation to express proteins that are incapable of oncogenic transformation and by codon optimization. The optimized HPV-16 E6 expressing gene may include a nucleotide sequence set forth in SEQ ID NO: 1. The optimized HPV-16 E7 expressing gene may include a nucleotide sequence set forth in SEQ ID NO: 2. The optimized HPV-18 E6 expressing gene may include a nucleotide sequence set forth in SEQ ID NO: 3. The optimized HPV-18 E7 expressing gene may include a nucleotide sequence set forth in SEQ ID NO: 4.

DNA constructs may be designed to include a fusion gene which may include an optimized HPV subsequence encoding at least one HPV antigen selected from a group consisting of: an HPV-16 E6 expressing gene set forth in SEQ ID NO: 1, an HPV-16 E7 expressing gene set forth in SEQ ID NO: 2, an HPV-18 E6 expressing gene set forth in SEQ ID NO: 3, and an HPV-18 E7 expressing gene set forth in SEQ ID NO: 4. In some embodiments, pBI-11, which has a nucleotide sequence set forth in SEQ ID NO: 5, is a DNA construct including a fusion gene which includes: a subsequence encoding a signal peptide; an optimized HPV subsequence encoding an HPV-16 E7 expressing gene set forth in SEQ ID NO: 2, an HPV-18 E7 expressing gene set forth in SEQ ID NO: 4, an HPV-16 E6 expressing gene set forth in SEQ ID NO: 1, and an HPV-18 E6 expressing gene set forth in SEQ ID NO: 3; and a subsequence encoding an HSP70. In some embodiments, pBI-12, which has a nucleotide sequence set forth in SEQ ID NO: 6, is a DNA construct comprising a fusion gene which includes: an optimized signal sequence encoding a signal peptide; an optimized HPV subsequence encoding an HPV-16 E7 expressing gene set forth in SEQ ID NO: 2, an HPV-18 E7 expressing gene set forth in SEQ ID NO: 4, an HPV-16 E6 expressing gene set forth in SEQ ID NO: 1, and an HPV-18 E6 expressing gene set forth in SEQ ID NO: 3; and a subsequence encoding an HSP70.

EXAMPLE 1: DESIGN AND SYNTHESIS OF HPV DNA VACCINE CONSTRUCTS

The pBI-1 DNA construct has been described previously as pNGVL4a-SigE7(detox)HSP70 (C. Trimple et al. *Vaccine* 2003, 21:4036-4042). In one example, the pBI-10.1 DNA construct was derived by Gibson assembly of a DNA fragment synthesized by Bio Basic (Markham, ON, Canada) encoding a fusion protein of the signal peptide, HPV-16 E7 (detox), HPV-18 E7 (detox), HPV-16 E6 (detox), and HPV-18 E6 (detox) as well as a 5' portion of HSP70 (up to the Tth111I site), flanked 5' by anEcoRI and Kozak site and 3' with a Tth111I site. The synthesized DNA fragment was cloned into the pBI-1 to replace the fragment between EcoRI and Tth111I in frame with HSP70.

Similar to pBI-10.1, the pBI-11 DNA construct included a synthesized DNA fragment encoding a fusion protein of the signal peptide, HPV-16 E7, HPV-18 E7, HPV-16 E6, and HPV-18 E6, and HSP70, but the expressing genes for HPV-16 E7, HPV-18 E7, HPV-16 E6, and HPV-18 E6 in pBI-11 were further codon-optimized. The pBI-12 DNA construct also included a synthesized DNA fragment encoding a fusion protein of the signal peptide, HPV-16 E7, HPV-18 E7, HPV-16 E6, and HPV-18 E6, and HSP70, but the expressing genes for the signal peptide, HPV-16 E7, HPV-18 E7, HPV-16 E6, and HPV-18 E6 in pBI-12, were further codon-optimized. The synthesized DNA fragment of pBI-11 or pBI-12 was cloned into the pBI-1 to replace the fragment between EcoRI and Tth111I in frame with HSP70.

The genes in the synthesized DNA fragment of each DNA construct that have been either optimized for gene expression (FIG. 1, fragments 101), mutated for detox (FIG. 1, fragments 102), or based on native papillomaviral sequences (FIG. 1, fragments 103), are shown in FIG. 1.

EXAMPLE 2: HPV ANTIGEN EXPRESSION LEVEL IS ENHANCED THROUGH CODON OPTIMIZATION

To determine whether cells transfected with the various DNA constructs appropriately produced the encoded antigen, western blot analysis was conducted. HEK 293 cells were transfected with 10 micrograms (μg) of one of pBI-1, pBI-10.1, pBI-11, or pBI-12 DNA constructs. After 48 hours of transfection, cell lysates were collected for western blot analysis, the results of which are illustrated in FIG. 2. pBI-1, pBI-10.1, pBI-11 or pBI-12 was separated on Precast Tris-HCl protein gel (Life Technology, Rockville, MD, USA) and then transferred on to nitrocellulose membrane (Bio-Rad Laboratories, Hercules, CA). After blocking, the membrane was hybridized with anti-HPV-16-E7 monoclonal antibody (denoted as HPV16 E7 ab in FIG. 2) (8C9 clone from Invitrogen, Thermo Fisher Scientific, Waltham, MA), anti-HPV-18/16-E6 (denoted as HPV18/16 E6 ab in FIG. 2) (CIP5 clone from Abcam PLC, Cambridge, UK) or anti-GAPDH (glyceraldehyde-3-phosphate dehydrogenase) (denoted as GAPDH in FIG. 2) (catalog number [no.] 60004-1-Ig; Proteintech® Group, Rosemont, IL) to characterize the expression of the fusion protein containing HPV-16 E7, the fusion protein containing HPV-16/18 E6, or GAPDH (Cat: 60004-1-Ig, Proteintech® Group, Rosemont, IL) as loading control. Antibody binding was detected using a peroxidase-conjugated sheep anti-mouse secondary antibody (Amersham™, Piscataway, NJ, USA) and chemiluminescence (ECL$^+$ detection kit; Amersham™, Piscataway, NJ, USA).

As indicated in the results shown in FIG. 2, all the DNA constructs showed the expression of a fusion protein that contains HPV-16 E7 antigen. Compared to the cells transfected with pBI-10.1, those cells transfected with pBI-11 and pBI-12 resulted in a higher HPV-16 E7 expression level, suggesting that the HPV-16 E7 expression level was successfully enhanced by the optimized HPV subsequence in pBI-11 and pBI-12.

Furthermore, HPV-16 E6 and/or HPV-18 E6 were detected in the cells transfected with either pBI-10.1, pBI-11 or pBI-12. In comparison, HPV-16 E6 and/or HPV-18 E6 expression levels in the cells transfected with pBI-11 and pBI-12 were higher than those in the cells transfected with pBI-10.1, indicating the optimized HPV subsequence of pBI-11 and pBI-12 enabled the cells to express HPV-16 E6 and HPV-18 E6 in an increased amount.

Taken together, the results suggested that the optimized HPV subsequences in pBI-11 and pBI-12 achieved an elevated expression level of HPV antigen.

EXAMPLE 3: CELLS TRANSFECTED WITH pBI-11 OR pBI-12 ARE ABLE TO ENHANCE PRESENTATION OF HPV ANTIGENIC PEPTIDE BY MHC CLASS I MOLECULES

To compare the capacity of HPV antigen presentation by cells transfected with either pBI-10.1, pBI-11, or pBI-12 DNA construct, in vitro T cell activation assays were performed.

Figure 3B:
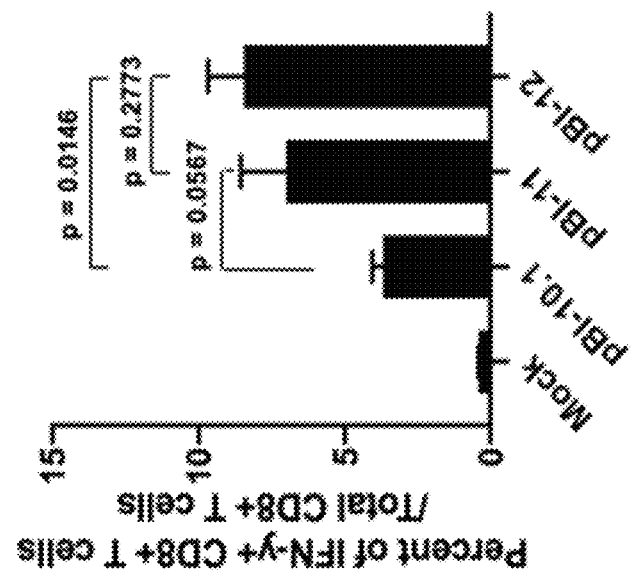
FIGS. 3A and 3B are bar charts comparing the percentage of IFN-γ$^+$ CD8$^+$ T cells/total CD8$^+$ cells of a control group, a pBI-10.1 group, a pBI-11 group and a pBI-12 group in the in vitro T cell activation assays using either murine H-2D$^b$-restricted HPV-16 E7 peptide (aa 49-57)-specific CD8$^+$ T cells (FIG. 3A) or H-2K$^b$-restricted HPV-18 E6 peptide (aa 67-75)-specific CD8$^+$ T cells (FIG. 3B) to compare the capacity of HPV antigen presentation by cells transfected with each of the DNA constructs, in accordance with an embodiment of the present disclosure.
Figure 3A:
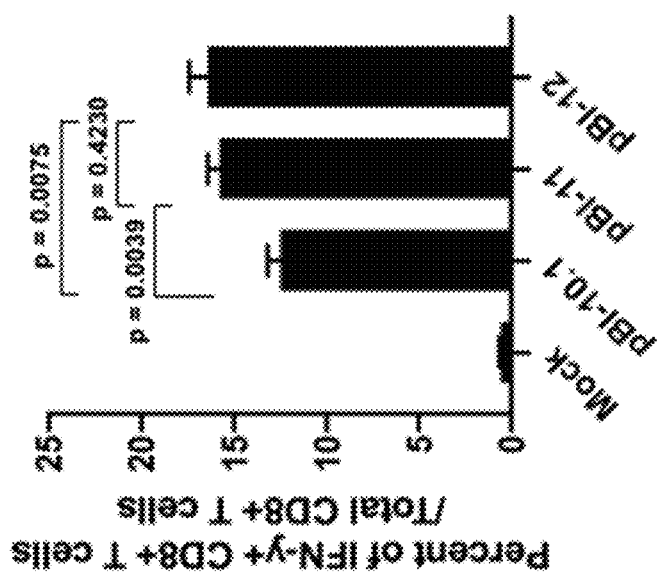

293-D$^b$ or 293 K$^b$ cells were transfected with either pBI-10.1, pBI-11, or pBI-12 DNA construct or mock transfected using Lipofectamine 2000. 24 hours later, these cells were harvested and cocultured with either murine H-2D$^b$-restricted HPV-16 E7 (aa 49-57) peptide-specific CD8$^+$ T cells (as depicted in FIG. 3A) or murine H-2K$^b$-restricted HPV-18 E6 (aa 67-75) peptide-specific CD8$^+$ T cells (as depicted in FIG. 3B) in the presence of GolgiPlug™ (BD Biosciences, San Diego, CA). The cells were then harvested, and IFN-γ intracellular staining was performed to determine the activation of HPV-16 E7 or HPV-18 E6 antigen-specific CD8$^+$ T cells.

As indicated in the results shown in FIGS. 3A and 3B, cells transfected with pBI-11 or pBI-12 were able to activate more HPV-16 E7 peptide (aa 49-57)-specific CD8$^+$ T cells and HPV-18 E6 peptide (aa 67-75)-specific CD8$^+$ T cells than cells transfected with pBI-10.1. Mock transfected cells did not generate any appreciable activation of HPV antigenic peptide (e.g., both E7 peptide (aa 49-57)-specific CD8$^+$ T cells and E6 peptide (aa 67-75)-specific CD8$^+$ T cells). Accordingly, the data showed that the enhanced expression of HPV-16/18 E6/E7 fusion protein in the cells transfected with pBI-11 or pBI-12 facilitated the presentation of HPV antigens by major histocompatibility complex (MHC) class I molecules to activate HPV antigen-specific CD8$^+$ T cells.

EXAMPLE 4: pBI-11 AND pBI-12 LEAD TO ENHANCED HPV-16 E7-SPECIFIC CD8$^+$ T CELL-MEDIATED IMMUNE RESPONSES

In vivo T cell activation assays were performed to compare immune response in mice vaccinated with either pBI-10.1, pBI-11, or pBI-12.

Figure 4B:
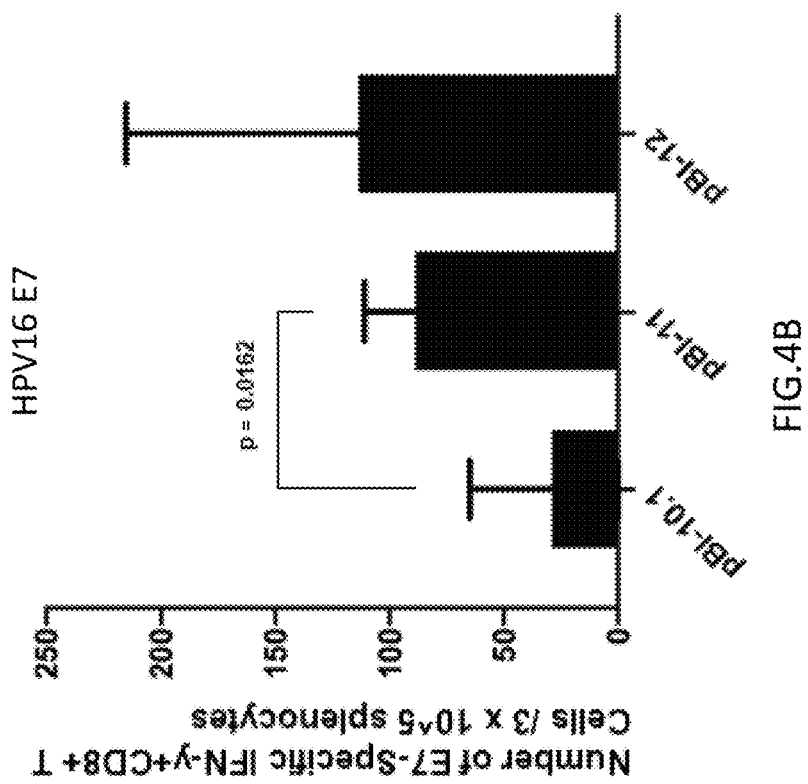
FIG. 4B is a bar chart comparing the number of HPV-16 E7-specific IFN-γ$^+$ CD8$^+$ T cells/3×10$^5$ splenocytes after the splenocytes prepared from mice vaccinated with either pBI-10.1, pBI-11, or pBI-12 being stimulated by HPV-16 E7 (aa 49-57) peptide, in accordance with an embodiment of the present disclosure.
Figure 4A:
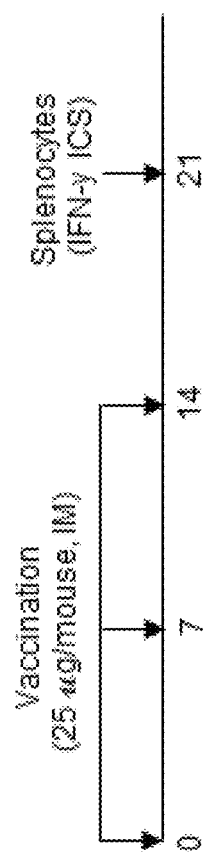
FIG. 4A is a schematic illustration of the experimental design for comparing HPV-16 E7-specific CD8$^+$ T cell responses generated by the various DNA constructs, in accordance with an embodiment of the present disclosure.

FIG. 4A is a schematic illustration of the experiment design. 6- to 8-week-old female C57BL/6 mice purchased from Taconic Biosciences (Germantown, NY) were vaccinated with 25 micrograms (μg)/mouse of either pBI-1, pBI-10.1, pBI-11, or pBI-12 DNA construct intramuscularly 3 times at 7-day intervals. One week after the last vaccination, splenocytes were collected for analysis of CD8$^+$ T cell response as determined by intracellular cytokine staining for interferon-γ followed by flow cytometry after stimulation with the known MHC-I peptides in HPV-16 E6 and E7 and HPV-18 E6.

As indicated in the results shown in FIG. 4B, both pBI-11 and pBI-12-vaccinated mice showed significantly higher E7-specific CD8$^+$ T cell-mediated immune responses than pBI-10.1-vaccinated mice. That is, pBI-11 and pBI-12, which include the optimized HPV subsequence, could induce enhanced antigen-specific CD8$^+$ T cell-mediated immune response in vivo.

Based on the fusion protein expression levels and the data of in vivo T cell activation assay, it is suggested that the enhanced expression of HPV antigen in cells transfected with pBI-11 or pBI-12, compared to that in cells transfected with pBI-10.1, due to codon optimization contributes to more potent T cell-mediated immune responses to the HPV antigens in the vaccinated mice.

EXAMPLE 5: pBI-11 DNA CONSTRUCT ELICITS A THERAPEUTIC ANTITUMOR RESPONSE IN AN HPV-16 E6/E7 EXPRESSION TUMOR MODEL, TC-1

The ability of the DNA construct of the present disclosure to generate therapeutic antitumor effects against HPV-associated diseases were examined in the HPV-16 E6/E7$^+$ TC-1 tumor model.

Figure 5A:
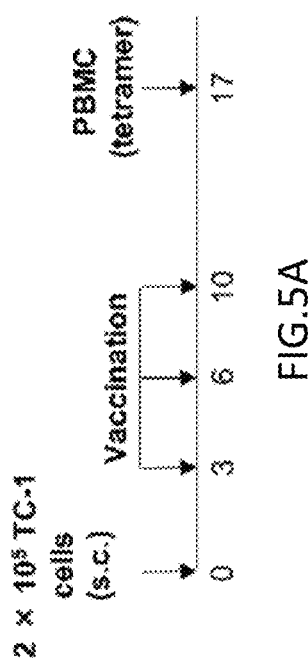
FIG. 5A is a schematic illustration of the experimental design of an in vivo tumor treatment experiment using HPV-16 E6/E7$^+$ TC-1 tumor model, in accordance with an embodiment of the present disclosure.

FIG. 5A is a schematic illustration of the experiment design. 6- to 8-week-old female C57BL/6 mice were injected with 2×10⁵ of TC-1 tumor cells subcutaneously on day 0. On days 3, 6, and 10, the tumor-bearing mice were either vaccinated with pBI-10.1, pBI-11 or pBI-12 (25 µg/50 microliters (ul)/mouse) through intramuscular (I.M.) injection or left untreated as a control. In some embodiments, alternative and/or additional vaccination, such as TA-HPV, could be used to vaccinate the mice as the boosting vaccine described herein.

One week after final vaccination, PBMCs were collected for tetramer staining. For tetramer staining, mouse PBMCs were stained with purified anti-mouse CD16/32 first and then stained with FITC-conjugated anti-mouse CD8a and PE-conjugated HPV-16 E7 (aa 49-57) peptide-loaded H-2D$^b$ tetramer or PE-conjugated HPV-18 E6 (aa 67-75) peptide-loaded H-2K$^b$ tetramer at 4° C. for 1 hour. After washing, the cells were stained with 7-AAD. The cells were acquired with the FACSCalibur™ flow cytometer and analyzed with CellQuest Pro software (BD Biosciences, Mountain View, CA). The results of tetramer staining are shown in FIGS. 5B and 5C.

The growth of the tumor was monitored twice a week by palpation and digital caliper measurement. Tumor volume was calculated using the formula [largest diameter×(perpendicular diameter)²]×3.14/6 and is shown in FIG. 5D. The survival rate of the tumor-bearing mice was recorded, as illustrated in FIG. 5E, where both natural death and a tumor diameter greater than 2 cm leading to death were counted as death.

Figure 5C:
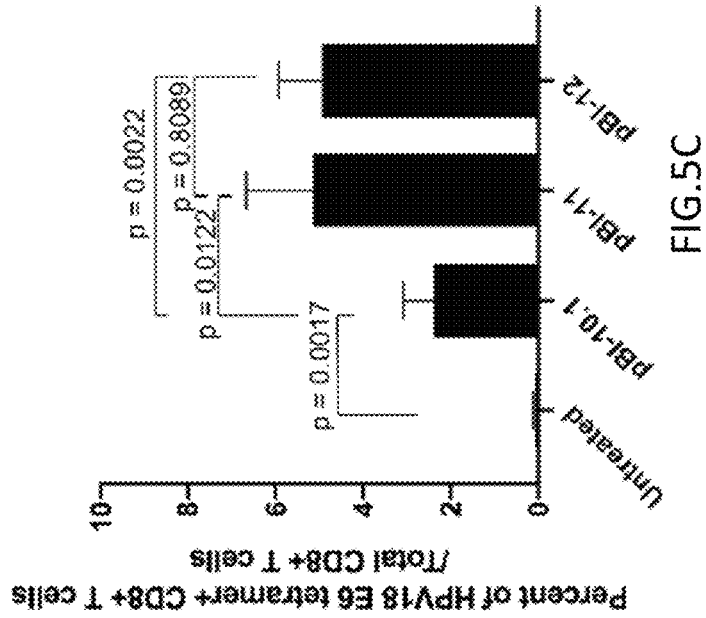
FIG. 5C is a bar chart showing the percentage of HPV-18 E6-specific CD8$^+$ T cells/total CD8$^+$ cells in PBMCs prepared from untreated mice or mice treated with pBI-10.1, pBI-11, or pBI-12 using HPV-18 E6 (aa 67-75) peptide-loaded tetramer staining, using a two-tailed Student's t-test, in accordance with an embodiment of the present disclosure.
Figure 5B:
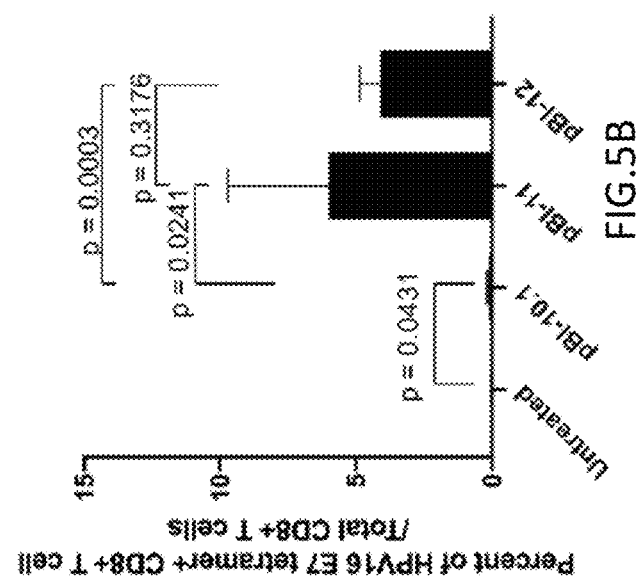
FIG. 5B is a bar chart showing the percentage of HPV-16 E7-specific CD8$^+$ T cells/total CD8$^+$ cells in peripheral blood mononuclear cells (PBMCs) prepared from untreated mice or mice treated with pBI-10.1, pBI-11, or pBI-12 using HPV-16 E7 (aa 49-57) peptide-loaded tetramer staining, using a two-tailed Student's t-test, in accordance with an embodiment of the present disclosure.
Figure 5E:
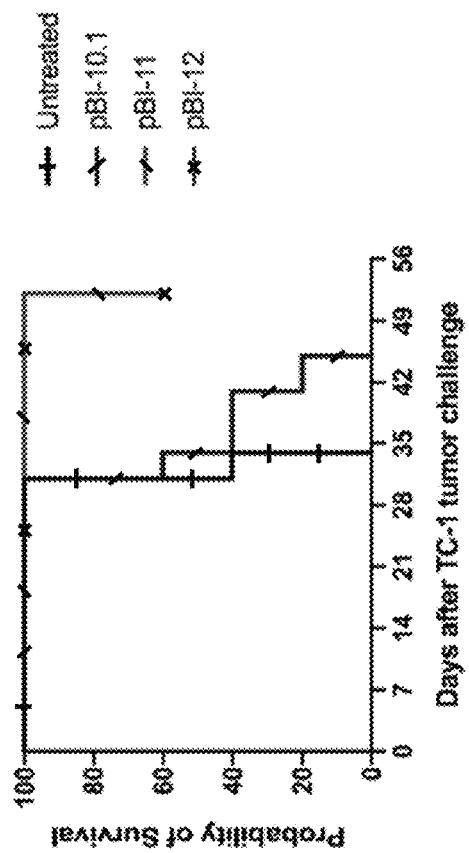
FIG. 5E is a Kaplan-Meier survival curve showing the probability of survival in the untreated mice and the mice treated with pBI-10.1, pBI-11, or pBI-12 in the in vivo tumor treatment experiment, in accordance with an embodiment of the present disclosure.
Figure 5D:
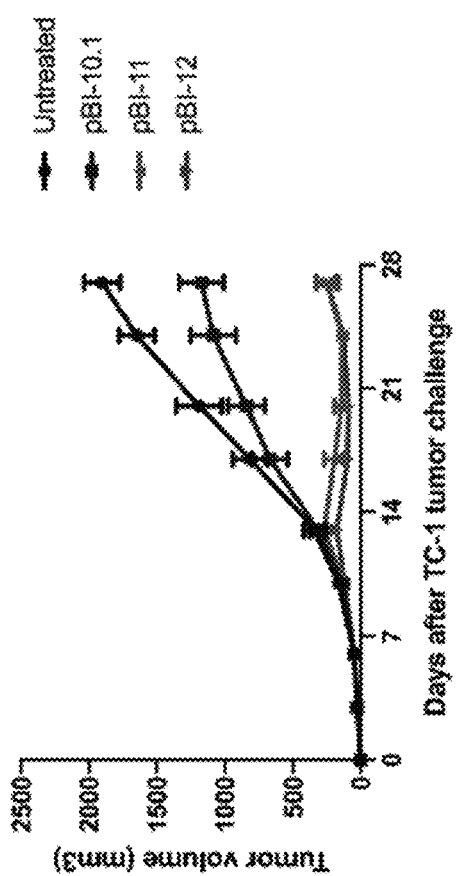
FIG. 5D is a curve chart showing TC-1 tumor volumes in the untreated mice and the mice treated with pBI-10.1, pBI-11, or pBI-12 in the in vivo tumor treatment experiment, in accordance with an embodiment of the present disclosure.

FIGS. 5B and 5C demonstrate that, compared to the untreated mice, tumor-bearing mice treated with pBI-10.1 showed HPV-16 E7-specific and HPV-18 E6-specific CD8⁺ T cell-mediated immune responses. Moreover, tumor-bearing mice treated with pBI-11 or pBI-12 further exhibited significantly higher HPV-16 E7-specific and HPV-18 E6-specific CD8⁺ T cell-mediated immune responses than mice vaccinated with pBI-10.1. Additionally, as shown in FIG. 5C, tumors in mice vaccinated with pBI-11 or pBI-12 grew significantly slower than in mice treated with pBI-10.1. Furthermore, vaccination with pBI-11 or pBI-12 also resulted in better survival than that for mice treated with pBI-10.1 (FIG. 5D). As a result, the present disclosure of the DNA vaccine including a DNA construct which includes a fusion gene having an optimized HPV subsequence, such as pBI-11 and pBI-12, can effectively enhance antitumor immune response against established TC-1 tumors and prolong survival of the tumor-bearing mice.

In conclusion, DNA vaccines having the optimized HPV subsequence encoding HPV-16 E6 (SEQ ID NO: 1), HPV-16 E7 (SEQ ID NO: 2), HPV-18 E6 (SEQ ID NO: 3), and/or HPV-18 E7 (SEQ ID NO: 4) of the present disclosure significantly induce enhanced HPV antigen expression and improved immune responses compared to DNA vaccines without the optimized HPV subsequence. It is surprising that the optimized HPV subsequence of the present disclosure successfully achieves a stronger antigen-specific immune response in vivo and further translates into more potent antitumor efficacy.

Those skilled in the art will readily observe that numerous modifications and alterations of the device and method may be made while retaining the teachings of the disclosure. Accordingly, the above disclosure should be construed as limited only by the metes and bounds of the appended claims.

What is claimed is:

1. A DNA vaccine, comprising:
a DNA construct comprising a fusion gene,
wherein the fusion gene includes an optimized human papillomavirus (HPV) subsequence encoding at least one HPV antigen, and
wherein the optimized HPV subsequence comprises one or more of:
an HPV-16 E6 expressing gene set forth in SEQ ID NO: 1,
an HPV-16 E7 expressing gene set forth in SEQ ID NO: 2,
an HPV-18 E6 expressing gene set forth in SEQ ID NO: 3, and
an HPV-18 E7 expressing gene set forth in SEQ ID NO: 4.

2. The DNA vaccine according to claim 1,
wherein the fusion gene further comprises a subsequence encoding an immunostimulant.

3. The DNA vaccine according to claim 2,
wherein the immunostimulant is a 70 kilodalton (kDa) heat shock protein (HSP70) or a human calreticulin (CRT) protein.

4. The DNA vaccine according to claim 2,
wherein the optimized HPV subsequence comprises the HPV-16 E6, HPV-16 E7, HPV-18 E6, and HPV-18 E7 expressing genes, and
wherein the fusion gene comprises SEQ ID NO: 5.

5. The DNA vaccine according to claim 2,
wherein the fusion gene further comprises an optimized signal sequence,
wherein the fusion gene comprises SEQ ID NO: 6.

6. A method for treating an HPV-associated disease in a subject in need thereof, comprising:
administering a DNA vaccine according to claim 1 to the subject.

7. The method according to claim 6, further comprising administering a recombinant vaccinia virus expressing E6 and E7 of both HPV-16 and HPV-18 to the subject, wherein the DNA vaccine is administered as a priming vaccine and the recombinant vaccinia virus expressing E6 and E7 of both HPV-16 and HPV-18 is administered as a boosting vaccine.

8. The method according to claim 7, wherein the recombinant vaccinia virus expressing E6 and E7 of both HPV-16 and HPV-18 is TA-HPV.

9. The method according to claim 8,
wherein the TA-HPV is administered at a dose ranging from $1 \times 10^4$ plaque-forming units (pfu) to $2 \times 10^8$ pfu.

10. The method according to claim 8,
wherein the DNA vaccine is administered at a dose ranging from 100 micrograms per subject to 20 milligrams per subject.

* * * * *